United States Patent
Teng et al.

(10) Patent No.: US 11,580,421 B2
(45) Date of Patent: Feb. 14, 2023

(54) WEAKLY SUPERVISED LEARNING FOR IMPROVING MULTIMODAL SENSING PLATFORM

(71) Applicant: Qualcomm Incorporated, San Diego, CA (US)

(72) Inventors: Diyan Teng, Santa Clara, CA (US); Rashmi Kulkarni, Menlo Park, CA (US); Justin McGloin, Los Altos, CA (US)

(73) Assignee: QUALCOMM Incorporated, San Diego, CA (US)

( * ) Notice: Subject to any disclaimer, the term of this patent is extended or adjusted under 35 U.S.C. 154(b) by 660 days.

(21) Appl. No.: 16/655,031

(22) Filed: Oct. 16, 2019

(65) Prior Publication Data

US 2021/0117818 A1   Apr. 22, 2021

(51) Int. Cl.
| | |
|---|---|
| *G06F 9/00* | (2006.01) |
| *G06N 5/04* | (2023.01) |
| *G06N 20/00* | (2019.01) |
| *G06F 9/4401* | (2018.01) |

(52) U.S. Cl.
CPC ............... *G06N 5/04* (2013.01); *G06N 20/00* (2019.01); *G06F 9/4401* (2013.01)

(58) Field of Classification Search
CPC .................................. G06N 5/04; G06N 20/00
USPC .......................................................... 706/12
See application file for complete search history.

(56) References Cited

U.S. PATENT DOCUMENTS

| | | | | |
|---|---|---|---|---|
| 2011/0215966 A1* | 9/2011 | Kim | ................ | H04W 52/0261 342/357.29 |
| 2011/0282828 A1* | 11/2011 | Precup | ................ | G06V 40/25 706/54 |
| 2011/0300875 A1* | 12/2011 | Kim | ................ | G01S 19/47 455/456.1 |
| 2015/0095678 A1* | 4/2015 | Nachman | ............. | G06F 1/3234 713/323 |
| 2016/0150072 A1* | 5/2016 | Rangarajan | ....... | H04W 52/0254 455/574 |
| 2016/0302148 A1* | 10/2016 | Buck | ................ | H04L 43/16 |
| 2017/0086732 A1* | 3/2017 | Tribble | ................ | A61B 5/6803 |
| 2017/0205863 A1* | 7/2017 | Lee | ................ | G06F 1/3206 |
| 2018/0240011 A1* | 8/2018 | Tan | ................ | G06N 3/084 |
| 2019/0187778 A1* | 6/2019 | Molnos | ................ | G06N 3/006 |
| 2019/0209022 A1* | 7/2019 | Sobol | ................ | A61B 5/7267 |
| 2019/0227528 A1* | 7/2019 | Abbott | ............... | G05B 19/4155 |

(Continued)

OTHER PUBLICATIONS

Zhang, Yivan, et al., "Learning from Indirect Observations," The University of Tokyo, RIKEN AIP, arXiv:1910.04394v1 [stat.ML], Oct. 10, 2019, pp. 1-19.

*Primary Examiner* — Volvick Derose
(74) *Attorney, Agent, or Firm* — Qualcomm Incorporated

(57) ABSTRACT

A machine learning model is trained for user activity detection and context detection on a mobile device. The machine learning model is configured to learn a statistical relationship between an always-on sensing modality of the mobile device and actual user context. Rather than user annotations, the machine learning model is enhanced and personalized for the always-on sensing modality by automated annotations obtained from non-always-on sensing modalities. The non-always-on sensing modality opportunistically provides an imperfect label of user context, where the imperfect label has a known associated probability of error.

19 Claims, 10 Drawing Sheets

(56) References Cited

U.S. PATENT DOCUMENTS

| | | | |
|---|---|---|---|
| 2019/0278354 A1* | 9/2019 | Alameh | G06F 3/013 |
| 2020/0133373 A1* | 4/2020 | Huang | G06F 3/017 |
| 2020/0204440 A1* | 6/2020 | Viswanathan | H04N 5/232 |
| 2020/0278738 A1* | 9/2020 | Madar, III | G06F 1/3206 |
| 2020/0303938 A1* | 9/2020 | Owen | H01M 10/44 |
| 2022/0021469 A1* | 1/2022 | Veijalainen | H04B 17/15 |

* cited by examiner

WEAKLY SUPERVISED LEARNING FOR IMPROVING MULTIMODAL SENSING PLATFORM

TECHNICAL FIELD

This disclosure relates generally to context detection in mobile devices and more particularly to improving and personalizing a machine learning model using a multimodal sensing platform for context detection in mobile devices.

DESCRIPTION OF RELATED TECHNOLOGY

A growing number of electronic devices are being programmed for context recognition and context awareness. In many instances, it is desirable for an electronic device to be aware of the environment in which it is located, the current activity of the user, the physiological state of the user, and/or the circumstances in which the user finds himself. For example, it may be desirable to know whether the user is on a plane, driving a car, in a meeting, or at a restaurant, and the electronic device may automatically adjust its functions or configurations according to the detected context. Awareness of "context" can help improve device usability as well as comfort and safety of use.

Many mobile devices, such as wearable electronic devices or smartphones, are built with a large number of sensors that can obtain real-time data of a device's surrounding environment. For example, a device's sensors may be able to ascertain the device's orientation and/or the user's motion. These sensors may be leveraged in classification algorithms to determine user context.

SUMMARY

The devices, systems, and methods of this disclosure each have several aspects, no single one of which is solely responsible for the desirable attributes disclosed herein.

One aspect of the subject matter of this disclosure can be implemented in a method of improving a machine learning model for use in context detection. The method includes receiving, at one or more processors of a mobile device, a first measurement x from a first input sensing modality group of the mobile device, where the first input sensing modality group includes a low-power sensing source, and receiving, at one or more processors of the mobile device, a second measurement z from a second input sensing modality group of the mobile device, where the second input sensing modality group includes a high-power sensing source. The method further includes determining, at the one or more processors of the mobile device, a label ŷ based on the second measurement z, where the label ŷ represents a predicted user context having an associated probability of error distribution Π, and updating a machine learning model using the label ŷ and the first measurement x, wherein the one or more processors are configured to continuously predict user context using the updated machine learning model.

In some implementations, the high-power sensing source is selected from a group consisting of: a high-resolution camera, a global positioning system (GPS), a cellular system, a Wi-Fi system, and a Bluetooth system. In some implementations, the low-power sensing source is selected from a group consisting of: an accelerometer, a gyroscope, a magnetometer, a light sensor, a proximity sensor, a low-resolution camera, a microphone or an audio sensor, an electrocardiogram (ECG), a photoplethysmogram (PPG), a temperature sensor, a respiration sensor, a compass, and a barometer. In some implementations, determining the label ŷ based on the second measurement z is determined using an independently trained inference model or classifier, where the independently trained inference model or classifier is a deterministic algorithm for measurements obtained from the second input sensing modality group. In some implementations, the machine learning model is configured to provide a true statistical relationship p(x|y) between measurements received from the first input sensing modality group and an actual user context. Updating the machine learning model includes calculating, at the one or more processors of the mobile device, a noise corrected estimator $q(x|y=s_i)$, where the noise corrected estimator $q(x|y=s_i)$ is based on an inverted probability of error distribution $\Pi^{-1}$ and a plurality of stored training set members in a training set, the plurality of stored training set members comprising: (i) stored measurements obtained from the first input sensing modality group of the mobile device, and (ii) stored labels of predicted user contexts obtained from measurements from the second input sensing modality group of the mobile device. Updating the machine learning model further includes retraining the machine learning model based on the noise corrected estimator $q(x|y=s_i)$. In some implementations, the method further includes storing the first measurement x and the label ŷ locally on the mobile device as a training set member in a training set, where updating the machine learning model is performed locally on the mobile device. In some implementations, updating the machine learning model occurs without user annotation.

Another innovative aspect of the subject matter described in this disclosure can be implemented in a mobile device. The mobile device includes a low-power sensing source configured to provide a first measurement x and a high-power sensing source configured to provide a second measurement z. The mobile device further includes one or more processors coupled to the low-power sensing source and to the high-power sensing source, where the one or more processors are configured to: receive the first measurement x from the low-power sensing source, receive the second measurement z from the high-power sensing source, determine a label ŷ based on the second measurement z, where the label ŷ represents a predicted user context having an associated probability of error distribution Π, and update a machine learning model using the label ŷ and the first measurement x.

In some implementations, the one or more processors are further configured to continuously predict user context using the updated machine learning model. In some implementations, the high-power sensing source is selected from a group consisting of: a high-resolution camera, a global positioning system (GPS), a cellular system, a Wi-Fi system, and a Bluetooth system, where the low-power sensing source is selected from a group consisting of: an accelerometer, a gyroscope, a magnetometer, a light sensor, a proximity sensor, a low-resolution camera, a microphone or an audio sensor, an electrocardiogram (ECG), a photoplethysmogram (PPG), a temperature sensor, a respiration sensor, a compass, and a barometer. In some implementations, the one or more processors are further configured to: store the first measurement x and the label ŷ locally on the mobile device as a training set member in a training set. In some implementations, the machine learning model is configured to provide a true statistical relationship p(x|y) between measurements received from the low-power sensing source and an actual user context. In some implementations, the one or more processors configured to update the machine learning model are configured to calculate a noise corrected estimator $q(x|y=s_i)$, where the noise corrected estimator $q(x|y=s_i)$ is based on an inverted probability of error distribution $\Pi^{-1}$ and a plurality of stored training set members in a training set, the plurality of stored training set members comprising: (i) stored measurements obtained from the low-power sensing source of the mobile device, and (ii) stored labels of predicted user contexts obtained from measurements from the high-power sensing source of the mobile device. The one or more processors configured to update the machine learning model are configured to retrain the machine learning model based on the noise corrected estimator $q(x|y=s_i)$.

BRIEF DESCRIPTION OF THE DRAWINGS

Details of one or more implementations of the subject matter described in this specification are set forth in the accompanying drawings and the description below. Other features, aspects, and advantages will become apparent from the description, drawings and claims. Note that the relative dimensions of the following figures may not be drawn to scale.

Like reference numbers and designations in the various drawings indicate like elements.

DETAILED DESCRIPTION

Figure 1:
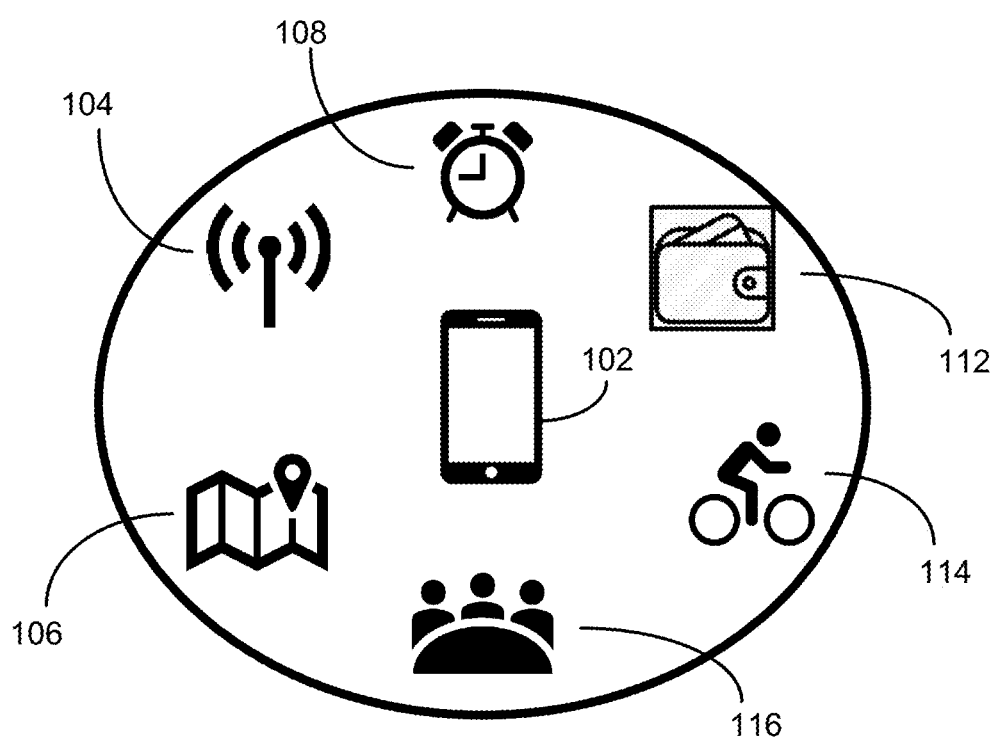
FIG. 1 shows a diagram illustrating an overall concept of context detection in mobile devices according to some implementations.

The following description is directed to certain implementations for the purposes of describing various aspects of this disclosure. However, a person having ordinary skill in the art will readily recognize that the teachings herein can be applied in a multitude of different ways. Various embodiments will be described in detail with reference to the accompanying drawings. References made to particular examples and implementations are for illustrative purposes, and are not intended to limit the scope of the claims.

The described implementations may be implemented in any device, apparatus, or system that includes a sensing system. In addition, it is contemplated that the described implementations may be included in or associated with a variety of electronic devices such as, but not limited to: mobile telephones, multimedia Internet enabled cellular telephones, mobile television receivers, wireless devices, smartphones, smart watches, smart cards, wearable devices such as bracelets, armbands, wristbands, rings, headbands, patches, belts, etc., Bluetooth devices, personal data assistants (PDAs), wireless electronic mail receivers, hand-held or portable computers, netbooks, notebooks, smart books, tablets, global navigation satellite system (GNSS) receivers/navigators, cameras, digital media players, camcorders, game consoles, wrist watches, electronic reading devices (e.g., e-readers), mobile health devices, etc. By way of example, the described implementations may be implemented in a smartphone. By way of another example, the described implementations may be implemented in a wearable device such as a health-monitoring device worn by a user. However, the wearable device may be capable of other applications, such as making/receiving phone calls, transmitting/receiving text messages, transmitting/receiving emails, keeping time, performing navigation, playing music, etc. By way of another example, the described implementations may be implemented in a tablet computer. Thus, the teachings are not intended to be limited to the implementations depicted solely in the Figures, but instead have wide applicability as will be readily apparent to one having ordinary skill in the art.

Smartphones, wearable devices, and other mobile devices are equipped with different sensors that can obtain information about a device's surrounding environment. Sensing a mobile device user's context may be highly useful in many intelligent use cases such as healthcare, drive assistance, and voice user interface (UI). For example, global positioning system (GPS) can be pre-activated and smartphone messaging can be disabled when a user's context shows that the user is driving. Speaker recognition can localize to different models depending on if the mobile device user's context indicates the user is in a meeting room or in a bus. Gesture/speech recognition can lead to different intentions depending on whether the user's location shows in a car, in a bedroom, or in a restaurant.

Contextual information may be determined from analysis of signals from different sensors, such as microphones, accelerometers, gyroscopes, magnetometers, light sensors, compasses, and low-resolution cameras, where such sensors may be part of a class of "always-on" sensing modalities or "low-power" sensing modalities. However, contextual information determined from "always-on" sensing modalities is typically insufficient in predicting user context to a high degree of certainty. More accurate predictions in user context can be achieved with multiple sensors of multiple sensing modalities. Parallel analysis of signals from multiple sensors may lead to a substantial increase in effectiveness of classification, but is attained at the expense of increased power consumption. Also, not every sensing modality is suitable to be activated all the time and not every sensing modality is useful in building an accurate inference model. Furthermore, many inference models use complex algorithms that drain substantial amounts of power, and many inference models do not generalize well to different users given a diverse population.

FIG. 1 shows a diagram illustrating an overall concept of context detection in mobile devices according to some implementations. A mobile device 102 may contain one or more sensing entities, sensing sources, or sensors that provide some raw data, feature, variables, or measurement that can be leveraged in determining user context. The mobile device 102 may contain one or more sensing sources for determining a radio-frequency (RF) environment 104. For instance, the mobile device 102 may connect to an external device or network by a Bluetooth, Wi-Fi, or cellular connection. The mobile device 102 may contain one or more sensing sources for determining location 106. By way of an example, the mobile device 102 may utilize a location-based sensor such as a GPS receiver. The mobile device 102 may contain one or more sensing sources for determining a time 108, where such determinations may be made by a clock. The mobile device 102 illustrates an example multimodal sensing platform.

The mobile device 102 may support context awareness or context recognition. As shown in FIG. 1, the context can include device position 112, where the device position 112 can indicate whether the mobile device 102 is in a purse, in a pocket, in the hand, etc. The context can additionally or alternatively include user activity 114, such as whether the user is walking, biking, jogging, running, talking on the phone, sleeping, etc. The context can additionally or alternatively include user environment 116, such as whether the user is in a meeting, at home, in the office, at a shopping mall, in a plane, in a car, on a bus, in a restaurant, etc.

In FIG. 1, the mobile device 102 may supplement data received from the one or more sensors (e.g., accelerometers, gyroscopes, and other always-on sensors) with determinations made regarding RF environment 104, location 106, and/or time 108. Ordinarily, the data from the one or more sensors alone is not sufficient to predict context such as device position 112, user activity 114, or user environment 116 with a high level of confidence. However, the determinations made regarding RF environment 104, location 106, and/or time 108 may add contextual information to enhance the level of confidence in predicting context. Some of these determinations may be made by non-always-on sensing modalities that can be opportunistically leveraged to enhance an inference algorithm, where the inference algorithm continuously predicts user context from an always-on sensing modality.

The present disclosure relates to continuously training a machine learning model for user context detection and recognition in a mobile device. Measurements made in always-on sensing modalities can be used in context detection on a regular basis, and measurements made in non-always-on sensing modalities can be opportunistically accessed when available. Measurements made in non-always-on sensing modalities can provide imperfect labels representing a predicted user context having some associated probability of error. In contrast to user annotations for improving the machine learning model, these imperfect labels function as noisy automated machine annotations for improving the machine learning model under a weakly supervised learning framework. Thus, the machine learning model is continuously improved and personalized for always-on sensing modalities in user context detection.

Particular implementations of the subject matter described in this disclosure may be implemented to realize one or more of the following potential advantages. Though the machine learning model collects data from sensing modalities that require high power, these sensing modalities are leveraged only opportunistically and when available. In other words, data collected from such sensing modalities may be accessed when the sensing modalities are being used for purposes other than training the machine learning model. Instead of constantly accessing costly, high-power sensing modalities that would drain substantial amounts of power, the present disclosure reduces power consumption by consulting the high-power sensing modalities when made available. And by accessing data from the high-power sensing modalities, the machine learning model can be trained by weakly supervised learning so that the performance and accuracy of the machine learning model for predicting user context is enhanced. In addition, the machine learning model automatically provides annotated data without requiring user input for annotation. Users may be unwilling to provide annotations. Training the machine learning model without user annotation improves user experience while making the process less burdensome and less time-consuming. Moreover, the machine learning model is trained using characteristics sensitive to individualized users so that the machine learning model is personalized to each user. This underscores the model being adapted for each user and not generalized to the population, thereby improving performance. Furthermore, training data is stored locally on the device and training algorithms are performed locally on the device, providing increased data privacy over conventional cloud-based solutions.

As used herein, the term "always-on sensing modality" refers to any particular type of sensing that continuously receives, collects, or tracks data on a user or a user's environment. Always-on sensing modalities continuously receive, collect, or track data for long stretches of time (e.g., few to several hours) with minimal burden on power consumption (e.g., less than 2% battery life consumed). Always-on sensing modalities may operate passively and automatically without necessitating user input to switch on/off the sensing modality. Always-on sensing modalities may continue to operate even in standby or sleep modes. Always-on sensing modalities may be characterized by low-power consumption. For example, always-on sensors may consume a few to tens of milliwatts (mW), such as power consumption that is less than about 100 mW, or between about 0.001 mW and about 99 mW. In contrast to non-always-on sensing modalities, always-on sensing modalities operate more regularly and are more frequently in use than non-always-on sensing modalities. The terms "always-on sensing modality," "low-power sensing modality," "frequently-used sensing modality," and "low-cost sensing modality" are used in this disclosure and are used interchangeably. Examples of sensors or information sources for always-on sensing modalities include but are not limited to: accelerometers, gyroscopes, magnetometers, light sensors, proximity sensors, low-resolution cameras, microphone or audio sensors, electrocardiogram (ECG), photoplethysmogram (PPG), temperature sensors, respiration sensors, compasses, and barometers.

The term "non-always-on sensing modality" refers to any particular type of sensing that receives, collects, or tracks data on a user or a user's environment for a limited period of time. Non-always-on sensing modalities may be disabled by users, as non-always-on sensing modalities are typically more sensitive to privacy than always-on sensing modalities. Non-always-on sensing modalities receive, collect, or track data with greater burden on power consumption than always-on sensing modalities. Non-always-on sensing modalities generally operate based on some user input to cause the sensing modality to be switched on/off. Non-always-on sensing modalities may be characterized by high-power consumption. For example, non-always-on sensors may consume hundreds of milliwatts of power, such as power consumption that is equal to or greater than about 100 mW, or between about 100 mW and about 5000 mW, or between about 200 mW and about 3000 mW. In contrast to non-always-on sensing modalities, always-on sensing modalities operate more regularly and are more frequently in use than non-always-on sensing modalities. The terms "high-power sensing modality," "infrequently-used sensing modality," and "high-cost sensing modality" are used in this disclosure and are used interchangeably. Examples of sensors or information sources for non-always-on sensing modalities include but are not limited to: global positioning systems (GPS), cellular systems, Bluetooth systems, and Wi-Fi systems. These systems may be used as non-always-on sensing modalities due to power concerns. GPS, cellular, Bluetooth, and Wi-Fi systems may include suitable transmitters, receivers, or transceivers for connectivity with external devices or networks. Another example of a sensor or information source for non-always-on sensing modalities include but is not limited to: high-resolution camera. The high-resolution camera may be used as a non-always-on sensing modality due to privacy and/or power concerns.

As used herein, "context" generally describes the environment in which the user is located, the current activity of the user, and/or the circumstances in which the user is in. The terms "context," "user context," "user activity," and "user environment" are used in this disclosure and are used interchangeably. To list some non-limiting examples, context may refer to the acoustic environment in which the user is located, the physical activity of the user, the transportation mode of the user, the mood of the user, and/or the physiological condition of the user.

As used herein, the term "context detection" refers to a device's ability to gather information and identify or predict a context of a user associated with the device. The terms "context detection," "context recognition," "context awareness," "activity detection," "activity recognition," and "activity awareness" are used in this disclosure and used interchangeably.

As used herein, the term "sensor" refers to any information source that can detect or measure a physical property or phenomena. In the present disclosure, sensors are used to detect or measure a physical property or phenomena of a user or user's context. The terms "sensor," "information source," or "sensing source" are used in this disclosure and are used interchangeably. "Always-on sensors," "low-power sensors," "frequently-used sensors," and "low-cost sensors" refer to sensors within a class of always-on sensing modalities. Likewise, "non-always-on sensors," "high-power sensors," "infrequently-used sensors," and "high-cost sensors" refer to sensors within a class of non-always-on sensing modalities.

As used herein, the term "mobile device" refers to any portable computing device or portable electronic device. The mobile device is generally carried, worn, or otherwise possessed by the user during activities of daily life. Examples include but are not limited to smartphones, tablets, and wearable devices. In the present disclosure, the mobile device is configured for context detection and includes sensors for always-on sensing modalities as well as sensors for non-always-on sensing modalities.

Always-on sensing can be used to detect user context on a regular basis. Inertial measurement units (IMUs) such as accelerometers, gyroscopes, and magnetometers, are examples of always-on sensors that can gather motion-related data on the user. For example, accelerometers may measure a user's acceleration and device orientation information and determine whether a user is standing still, walking, jogging, or running. A mobile device may include a baseline model or generic inference algorithm that is trained offline for a general population of users. The baseline model may predict context using the data gathered from always-on sensing. However, the baseline model is not necessarily tailored to the behaviors, patterns, and/or movements of the particular user associated with the mobile device. Training the baseline model to account for variations across a large population containing different demographics and types of individuals would require an extraordinary amount of resources that may be unrealistic. Though power consumption is relatively low, context detection using such baseline models are typically not very accurate and not personal.

Figure 2:
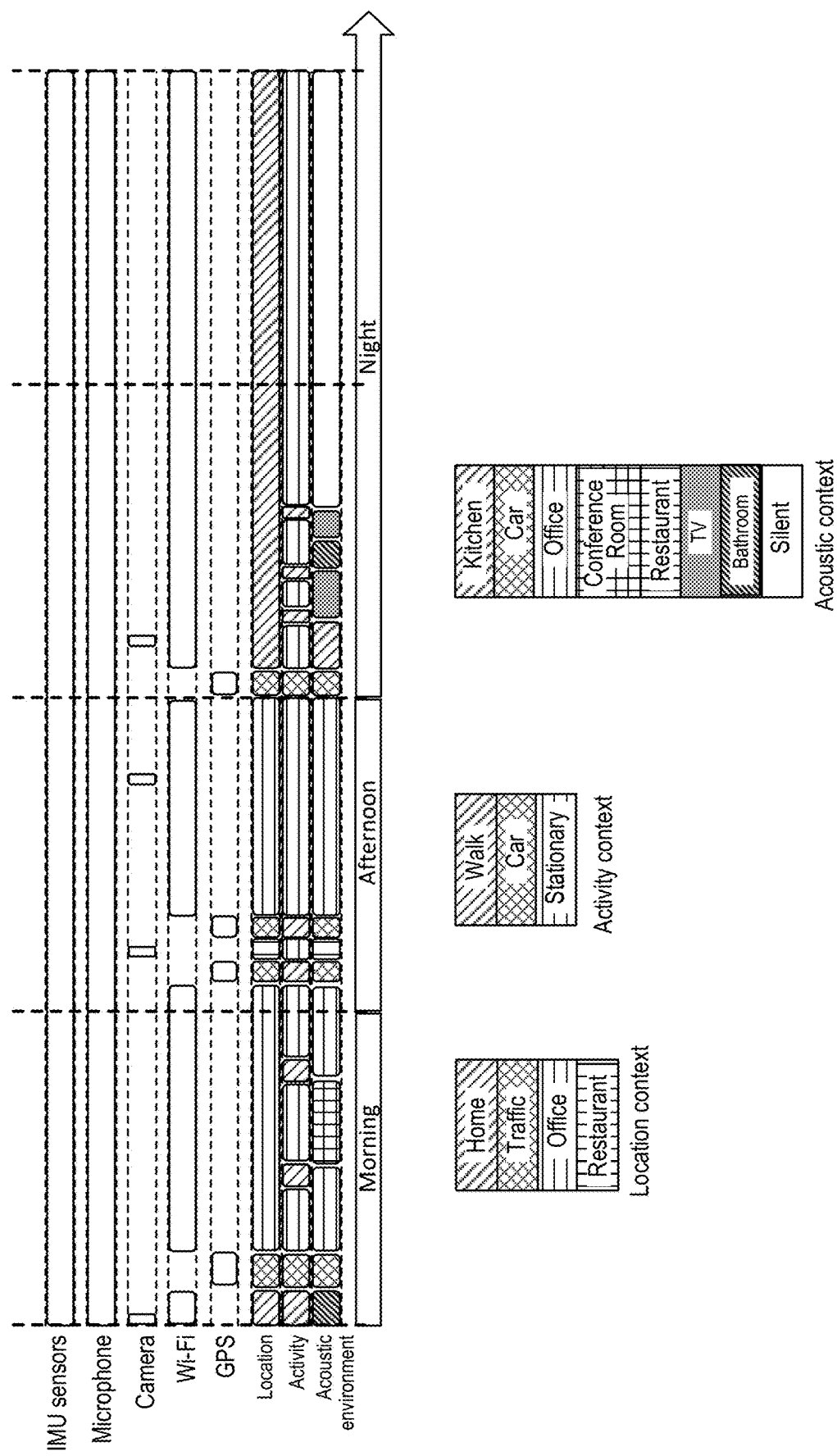
FIG. 2 shows an example timing diagram of a user's environments and activities during the course of a day in conjunction with usage of various functions of the user's mobile device.

Non-always-on sensing may also be used to help determine context. Location-based sensors, such as GPS, may supply navigation, speed, and location data that is useful for determining context. Connections to external devices or networks via Bluetooth, Wi-Fi, or cellular may also be useful in providing contextual information for determining context. Usage of a high-resolution camera may further be useful in ascertaining user context. FIG. 2 shows an example timing diagram of a user's environments and activities during the course of a day in conjunction with usage of various functions of the user's mobile device. As shown in FIG. 2, a user may occupy different locations including being at home, being in an office, being in a restaurant, or being on the road. Within the location, the user may occupy different acoustic environments. Specifically, the user may be in the kitchen at home, in a car while on the road, in an office, in a conference room in the office, at a restaurant, in front of a television, in a bathroom, or in a silent area. The user may also perform different activities such as walking, driving, or being stationary. The user may transition between different activities and different environments over the course of time. Certain functions of the user's mobile device may be turned activated/deactivated depending on the user's activities and/or environments. For example, the user may access the mobile device's Wi-Fi network while at home or in the office. The user may use GPS while traveling on the road. The user may use a high-resolution camera when stationary and when in a restaurant or while at home. In FIG. 2, usage of certain functions in non-always-on sensing modalities is at least partially indicative of certain user activities and environments. Non-always-on sensing modalities may provide contextual information that can be leveraged to improve context predictions.

Generic or public models using always-on sensing modalities may not be able to effectively distinguish between certain activities and environments. Data from non-always-on sensing modalities may be utilized without constantly activating them and without simply confirming/correcting a predicted user context at the moment of prediction. The present disclosure opportunistically leverages the non-always-on sensing modalities when available. Furthermore, the present disclosure adapts a machine learning model based on an always-on sensing modality for improved decision-making on user context. In other words, data from the non-always-on sensing modalities are not necessarily used to confirm/correct each prediction of user context, but used to improve a machine learning model based on low-power sensor readings. This provides a machine learning model that is personalized to the user. The machine learning model is trained by a weakly supervised framework using automated machine annotations rather than user annotations. Without interfering with user experience, the automated machine annotations provide imperfect annotations with some probability of error. An error correction mechanism in the present disclosure can account for the imperfect annotations to approximate a correct predictive model given enough training data sets. The training may occur locally on the mobile device for increased data privacy and reduced network latency.

Figure 3:
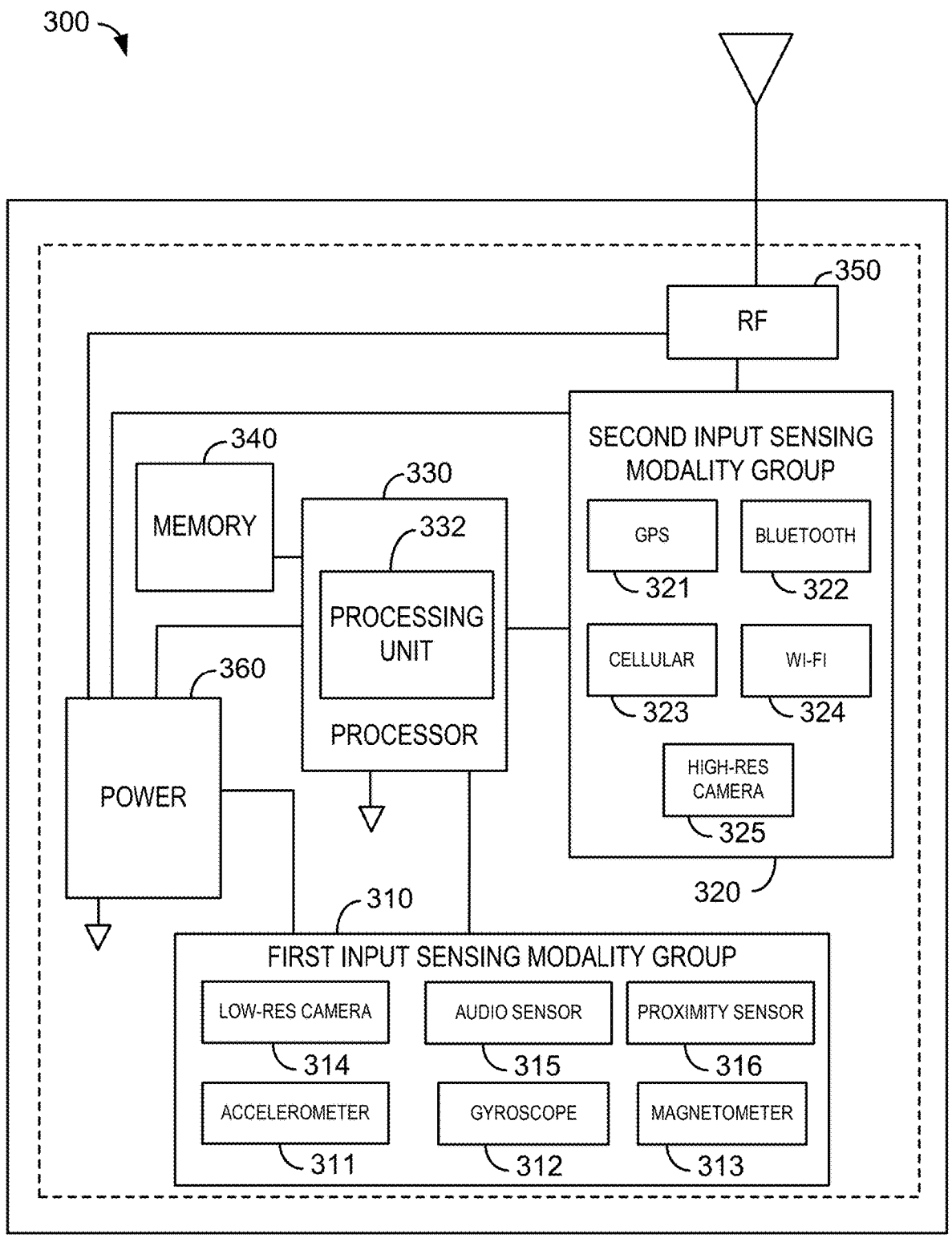
FIG. 3 shows a block representation of components of an example mobile device configured for context detection according to some implementations.

FIG. 3 shows a block representation of components of an example mobile device configured for context detection according to some implementations. The number of elements and types of elements shown in FIG. 3 are merely by way of example. Other implementations may have more, fewer, or different elements. The mobile device in FIG. 3 may be used to implement various steps, methods, and techniques for improving a machine learning model in context detection. In the implementation in FIG. 3, a mobile device 300 includes one or more low-power sensing sources in a first input sensing modality group 310, one or more high-power sensing sources in a second input sensing modality group 320, a processor 330, a memory 340, an RF antenna 350, and a power supply 360.

In some implementations, the first input sensing modality group 310 includes an accelerometer 311, a gyroscope 312, a magnetometer 313, a low-resolution camera 314, a microphone or audio sensor 315, and a proximity sensor 316. It will be understood that the first input sensing modality group 310 of the mobile device 300 may include more, fewer, or different low-power sensing sources. In FIG. 3, the accelerometer 311, the gyroscope 312, the magnetometer 313, the low-resolution camera 314, the microphone or audio sensor 315, and the proximity sensor 316 serve as examples of low-power sensing sources of the mobile device 300. The accelerometer 311 may be used to obtain acceleration data of a user. The gyroscope 312 may be used to obtain measurements of angular acceleration, angular velocity, or rotation. The magnetometer 313 may be used to obtain measurements of magnetic field or force. One or both of the gyroscope 312 and the magnetometer 313 can provide orientation of the user. The accelerometer 311, the gyroscope 312, and/or the magnetometer 313 may be able to provide other motion-related data, such as the type of motion, the direction of motion, the position of the mobile device 300, instantaneous and average velocities and accelerations of the user, etc. In some implementations, the mobile device 300 includes each of the accelerometer 311, the gyroscope 312, and the magnetometer 313, meaning that the mobile device 300 is equipped with all of the aforementioned IMUs. In some other implementations, the mobile device 300 includes a subset of the accelerometer 311, the gyroscope 312, and the magnetometer 313.

The mobile device 300 may further include a low-resolution camera 314, where the low-resolution camera 314 may be used to provide image data of a surrounding environment of the mobile device 300. The mobile device 300 may further include a microphone or audio sensor 315, where the microphone or audio sensor 315 may provide audio data picked up from the surrounding environment of the mobile device 300. The mobile device 300 may further include a proximity sensor 316, where the proximity sensor 316 may provide proximity data for sensing nearby objects in the surrounding environment. It will be understood that the mobile device 300 may alternatively or additionally include other low-power sensing sources such as light sensors, ECGs, PPGs, temperature sensors, respiration sensors, compasses, and barometers.

In some implementations, the second input sensing modality group 320 includes a GPS system 321, a Bluetooth system 322, a cellular system 323, a Wi-Fi system 324, and a high-resolution camera 325. It will be understood that the second input sensing modality group 320 of the mobile device 300 may include more, fewer, or different high-power sensing sources. In FIG. 3, the GPS system 321, the Bluetooth system 322, the cellular system 323, the Wi-Fi system 324, and the high-resolution camera 325 serve as examples of high-power sensing sources of the mobile device 300. The GPS system 321, the Bluetooth system 322, the cellular system 323, and the Wi-Fi system 324 may include wireless components such as a transmitter, receiver, or transceiver for wireless connection to an external device or network. Circuitry for the GPS system 321, the Bluetooth system 322, the cellular system 323, and the Wi-Fi system 324 may support communication in different frequency bands. Other frequency bands may be supported. In some implementations, the circuitry for the GPS system 321, the Bluetooth system 322, the cellular system 323, and/or the Wi-Fi system 324 may be connected to the RF antenna 350 for wireless communication with the external device or network.

The low-power sensing sources of the first input sensing modality group 310 and the high-power sensing sources of the second input sensing modality group 320 may be coupled to the processor 330. The processor 330 may receive data (e.g., raw data) from the low-power sensing sources and/or the high-power sensing sources. The processor 330 may be dedicated hardware specifically adapted to perform a variety of functions for the mobile device 300. In some implementations, the processor 330 may be or may include a programmable processing unit 332 that may be programmed with processor-executable instructions. In some implementations, the processor 330 may be a programmable microprocessor, microcomputer, or multiple processor chip(s) that can be configured by software instructions to perform a variety of functions for the mobile device 300. In some implementations, the processor 330 may be a combination of dedicated hardware and a programmable processing unit 332.

Using data received from the low-power sensing sources, the processor 330 may be configured to predict user context. Using data received from the high-power sensing source when a high-power sensing source is accessed by the mobile device 300, the processor 330 may be configured to train a machine learning model for user context detection governed by weakly supervised learning. The data received from the high-power sensing source may provide imperfect annotations of predicted user context and may not necessarily reflect actual user context. However, the imperfect annotations may have an associated with a probability of error distribution so that a statistical probability of error can be accounted for in training the machine learning model. Specifically, a noise corrected estimator may be calculated using the processor 330 that guarantees lossless recovery of the true statistical relationship between measurements received from low-power sensing sources and actual user context as sample size increases. Accordingly, the processor 330 may train the machine learning model based on the noise corrected estimator. A more detailed description of training/improving the machine learning model using a weakly supervised framework is provided below.

In some implementations, a memory 340 may store processor-executable instructions as well as data obtained from the first input sensing modality group 310 and the second input sensing modality group 320. In some implementations, the memory 340 may be a volatile memory, non-volatile memory (e.g., flash memory), or a combination thereof. In some implementations, the memory 340 may include internal memory included in the processor 330, memory external to the processor 330, or a combination thereof. The memory 340 may be coupled to the processor 330. In some implementations, the memory 340 may store training set members of a training set, where each of the training set members include: (i) a measurement obtained from a low-power sensing source, and (ii) an imperfect label of predicted user context determined from a measurement from a high-power sensing source. In addition, the memory 340 may store algorithms for determining or predicting user context, such as inference algorithms for determining imperfect labels from measurements obtained from high-power sensing sources and inference algorithms for determining user context from measurements obtained from low-power sensing sources. In some implementations, such inference algorithms may be public inference models or classifiers. In some implementations, the memory 340 may store training algorithms for improving a machine learning model for context detection, where such training algorithms may arrive at a correct generative model for determining user context from low-power sensing modalities. The memory 340 may enable localized storage of data from low- and high-power sensing sources, training sets, machine learning models or classifiers for predicting user context, and training algorithms for improving machine learning models. In some implementations, the processor 330 may execute machine learning models and training algorithms for improving machine learning models. The processor 330 may access processor-executable instructions from the memory 340. That way, training machine learning models for predicting user context can occur locally on the mobile device 300.

In some implementations, the low-power sensing sources of the first input sensing modality group 310, the high-power sensing sources of the second input sensing modality group 320, the processor 330, the memory 340, the RF antenna 350, and any other electronic components of the mobile device 300 may be powered by the power supply 360. The power supply 360 may be a battery, a solar cell, or other suitable power source for harvesting power.

Figure 4:
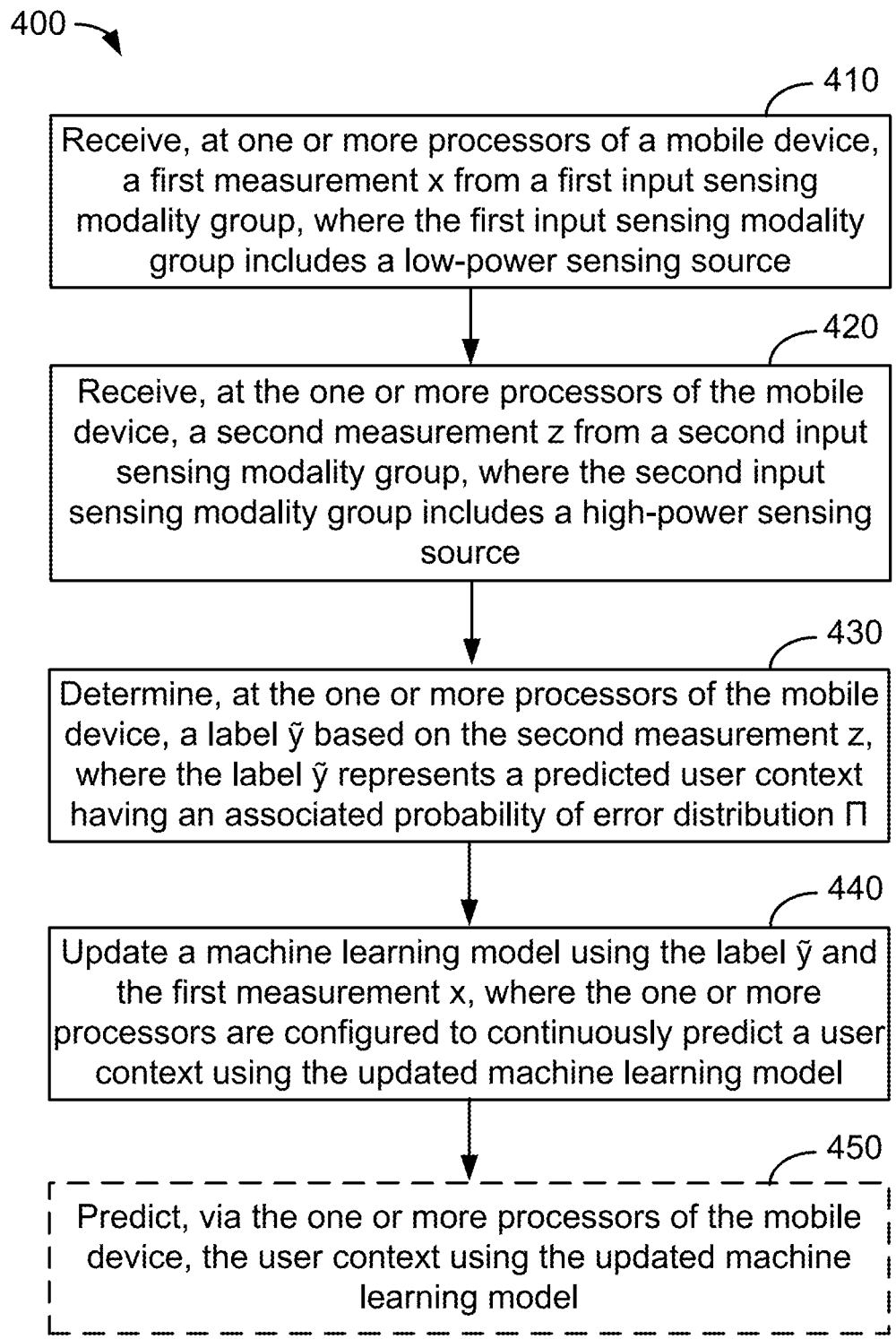
FIG. 4 shows a flow diagram illustrating an example process for improving a machine learning model for use in context detection according to some implementations.

FIG. 4 shows a flow diagram illustrating an example process for improving a machine learning model for use in context detection according to some implementations. A process 400 may be performed in a different order or with different, fewer, or additional operations. The blocks of the process 400 may be performed by one or more processors of a mobile device. In some implementations, the blocks of the process 400 may be performed by a mobile device as shown in FIG. 3. In some implementations, the blocks of the process 400 may be implemented, at least in part, according to software stored on one or more non-transitory computer readable media. Aspects of the process 400 are described with respect to FIGS. 5A-5B, 6, 7, and 8A-8E.

At block 410 of the process 400, a first measurement x is received at one or more processors of a mobile device from a first input sensing modality group. The first input sensing modality group includes a low-power sensing source or low-power sensor. The first input sensing modality group represents a class of always-on sensing modalities that receive, collect, or track data for long stretches of time with minimal burden on power consumption. Always-on sensing modalities are described earlier herein. Always-on sensing sources or low-power sensing sources of the first input sensing modality group may be coupled to the one or more processors of the mobile device. Examples of low-power sensing sources include but are not limited to accelerometers, gyroscopes, magnetometers, light sensors, proximity sensors, low-resolution cameras, microphones or audio sensors, ECGs, PPGs, temperature sensors, respiration sensors, compasses, and barometers.

The low-power sensing source may provide a first measurement x to the one or more processors. As used herein, any measurement "x" represents an independent measurement from a low-power sensing source of an always-on sensing modality. The first measurement x can thus provide data such as speech data, image data, face data, proximity data, ambient light data, temperature data, orientation data, motion kinetics data, and other information that can be obtained from the low-power sensing source. For example, the first measurement x can provide the speed of the user. The first measurement x is generally user dependent.

The low-power sensing source may continuously provide measurements "x." Because the first input sensing modality group provides always-on sensing, measurements "x" may be continuously provided or at least provided for long stretches of time. That way, several measurements "x" may be made over the course of time. Each measurement "x" may be indicative of user context. During the course of time, the low-power sensing source may detect changes in data, which may be indicative of changes in user context.

A simple algorithm or classifier may be configured to predict user context based on measurement "x." As used herein, such a simple algorithm or classifier may also be referred to as a "public model," "baseline model," or "baseline inference model." However, such predictions of user context may not necessarily be accurate. Put another way, predicted user context does not necessarily reflect an actual user context "y." As used herein, the actual user context "y" may also be referred to as "ground truth" or "true user context." The baseline model is not able to accurately predict the ground truth based on measurements "x." However, machine learning can train the baseline model to more accurately predict user context.

A baseline model of the present disclosure can be trained by weakly supervised learning to more accurately predict user context, where the baseline model predicts user context using measurements received from the low-power sensing source. The baseline model can be a machine learning model that can learn a statistical relationship between the first measurement x and actual user context y. The statistical relationship between the first measurement x and the actual user context y can be modeled in a generative distribution $p(x|y)$. The generative distribution $p(x|y)$ is a statistical model of a joint probability distribution for a given observable variable "x" and a target variable "y."

Machine learning models are usually divided into three broad categories: supervised learning, unsupervised learning, or reinforcement learning. In supervised learning, the training datasets are fully labeled, which means that there is a known relationship between the feature vector and the target variable. The objective is to learn this relationship so that it can be generalized to predict the target variable when it is missing. Examples of machine learning algorithms that are supervised include but are not limited to linear regression, logistic regression, decision trees, support vector machine (SVM), naive Bayes, k-nearest neighbors, and neural networks (multilayer perception). In unsupervised learning, the training data only consists of feature vectors. The objective is to explore the structure of the data. The structure can be statistical or geometrical, which can help represent the data in a succinct yet meaningful way. Examples of machine learning algorithms that are unsupervised includes k-means, Gaussian mixture model (GMM), Principal Components Analysis (PCA), and manifold learning. Meanwhile, the method of semi-supervised learning targets the problem where the training data is labeled partially. It combines the techniques in supervised learning to exploit the information in the label with the techniques in semi-supervised learning to incorporate the data structure revealed by the unlabeled part of the dataset. Finally, reinforcement learning refers to the problem of learning a set of rules about how to interact with an unknown environment. The dataset in reinforcement learning is obtained by allowing the agent to interact with the environment, which will give some feedback or reward the agent. The agent may further leverage the experience in the past to optimize the action it should take when faced with similar situation in the future. Examples of reinforcement learning techniques include model-based methods such as Markov Decision Process (MDP), and model-free methods such as Monte Carlo learning and Temporal Difference learning.

Weakly supervised learning can be considered another category of machine learning and may fall under one of three categories, though the definition of weakly supervised learning varies in literature. One type of weakly supervised learning is semi-supervised learning as described above. Another type of weakly supervised learning is positive-unlabeled learning, where only part of the instances from a positive hypothesis are labeled. Another type of weakly supervised learning is categorized as labeling with label "noise." Specifically, even though an output is labeled, the training instances may not be perfectly supervised. The label for the training instance has an associated probability of error so that a learner does not have direct access to ground truth. Weakly supervised learning in the present disclosure largely falls under this final category.

The label in the weakly supervised framework of the present disclosure may be referred to as an "imperfect" label or "noisy" label. This means that the label has an associated probability of error with respect to a label that reflects ground truth. Accordingly, there is some uncertainty associated a noisy label. The noisy label may be used in a training dataset for training the machine learning model of the present disclosure. The noisy label may be generated from non-always-on sensing modalities when available so that the noisy label may be provided as a machine automated annotation rather than by a user.

At block 420 of the process 400, a second measurement z is received at the one or more processors of the mobile device from a second input sensing modality group. The second input sensing modality group includes a high-power sensing source. The second input sensing modality group represents a class of non-always-on sensing modalities that receive, collect, or track data on a user or user's environment for a limited period of time. Non-always-on sensing modalities are described earlier herein. Non-always-on sensing sources or high-power sensing sources of the second input sensing modality group may be coupled to the one or more processors of the mobile device. Examples of high-power sensing sources include but are not limited to a high-resolution camera, GPS, cellular, Bluetooth, and Wi-Fi systems.

The high-power sensing source may provide a second measurement z to the one or more processors. As used herein, any measurement "z" represents an independent measurement from a high-power sensing source of an always-on sensing modality. By way of example, the second measurement z can provide data such as speed data, location data, connectivity information, and high-resolution image data. The second measurement z is usually invariant and insensitive to user identity.

Obtaining the second measurement z from the high-power sensing source may be leveraged opportunistically when the high-power sensing source is accessible. As a result, measurements "z" may be provided when the high-power sensing source is available, meaning that the high-power sensing source is being used or otherwise activated. Measurements "z" may provide additional contextual information along with measurements "x" in a multimodal sensing platform. Data from always-on sensing modalities and data from non-always-on sensing modalities may be leveraged to enhance a machine learning model for predicting user context.

At block 430 of the process 400, a label ŷ is determined at the one or more processors of the mobile device based on the second measurement z. The label ŷ represents a predicted user context having an associated probability of error distribution Π. Though the label ŷ reflects the predicted user context, such as driving or walking, the label ŷ is not certain that the predicted user context is the actual user context y. There may be some discrepancy or probability of error in statistics between the predicted user context in the label ŷ and the actual user context y. The probability of error in statistics is reflected in the probability of error distribution Π, which may also be referred to as a "confusion matrix" Π.

The label ŷ is determined from the second measurement z. An inference algorithm takes the second measurement z as input and predicts the predicted user context as the label ŷ. Determining the label ŷ may be determined using an independently trained inference model or classifier. The independently trained inference model or classifier may be a deterministic algorithm for any measurement "z" obtained from the second input sensing modality group. This means that given a particular second measurement z as an input, the output for the label ŷ will always be the same in a deterministic algorithm. Furthermore, the inference model for determining the label ŷ from the second measurement z is trained independently. This means that the inference model is trained separately beforehand and fixed, where the inference model may be trained separately by outside experts, researchers, designers, users, etc. The independently trained inference model or classifier may also be denoted "g(•)" in the present disclosure.

The associated probability of error distribution Π may be provided with the independently trained inference model or classifier. In particular, the associated probability of error distribution Π may be provided by a designer of the independently trained inference model through empirical evaluation on some validation dataset. The probability of error distribution Π may be presented as a matrix or table showing the performance of the independently trained inference model or classifier in terms of statistical probabilities. Each row of the matrix or table can represent the predicted user context, and each column of the matrix or table can represent the actual user context, or vice versa. The matrix or table of the associated probability of error distribution Π may be a proper left stochastic matrix. Alternatively, the matrix or table of the associated probability of error distribution $\Pi_R$ may be a proper right stochastic matrix. The matrix or table of the associated probability of error distribution Π is invertible. In some implementations, the probability of the predicted user context correctly predicting the actual user context is better than a random guess. For example, in a binary (two-class) problem, the probability of the predicted user context correctly predicting the actual user context is greater than 50%. Otherwise, the independently trained inference model or classifier will not improve a machine learning model for context detection.

An example associated probability of error distribution Π for a GPS speed reading is shown below in Table 1. Correct predictions are located along the diagonal of the table, indicating a 76% probability of correctly predicting phone calls in GPS speed readings, a 72% probability of correctly predicting slow walks in GPS speed readings, and a 100% probability of correctly predicting biking in GPS speed readings. In addition, there is a 24% probability of mistakenly predicting slow walk when the user is actually making a phone call, and there is a 28% probability of mistakenly predicting that the user is making a phone call when the user is actually slow walking.

TABLE 1

| | | Predicted User Context ($\tilde{y}$) | | |
| --- | --- | --- | --- | --- |
| | | Phone Call | Slow Walk | Biking |
| Actual | Phone Call | 0.76 | 0.24 | 0 |
| User | Slow Walk | 0.28 | 0.72 | 0 |
| Context (y) | Biking | 0 | 0 | 1 |

Figure 5A:
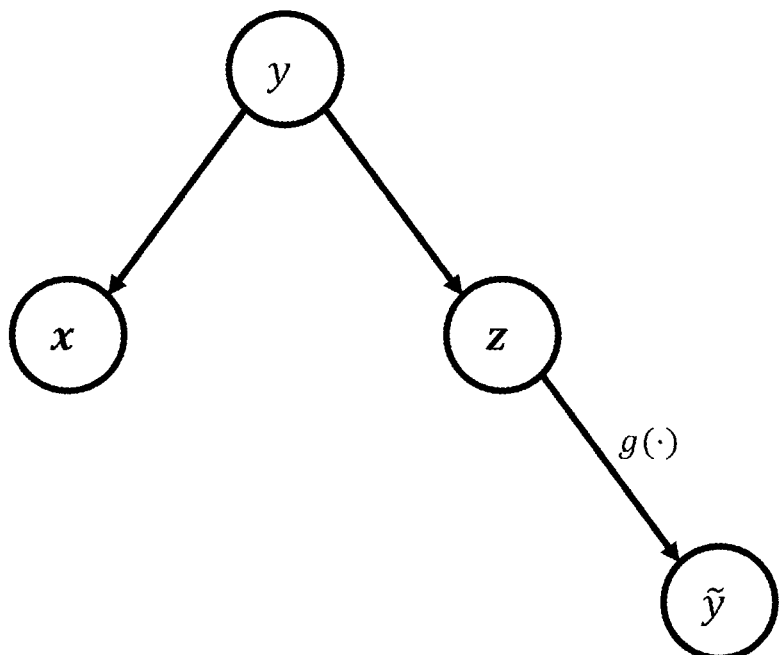
FIG. 5A shows an example conceptual model of a weakly supervised framework for obtaining information about a ground truth label based on two independent measurements according to some implementations.

FIG. 5A shows an example conceptual model of a weakly supervised framework for obtaining information about a ground truth label based on two independent measurements according to some implementations. The ground truth label y may have a value contained in a set of discrete and finite values $\{s_1, s_2, \ldots, s_k\}$. For example, the set of discrete and finite values may reflect different user contexts such as driving, walking, jogging, running, standing, sitting, talking on the phone, sleeping, and swimming, among other activities. A first measurement x may be obtained from an always-on sensing modality group and a second measurement z may be obtained from a non-always-on sensing modality group. The first measurement x and the second measurement z represent two independent measurements that contain class conditional information about the ground truth label y.

Figure 5B:
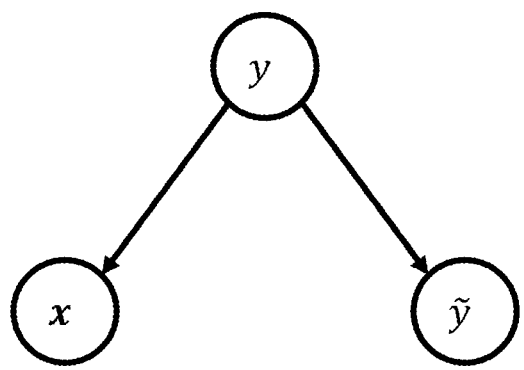
FIG. 5B shows example conceptual model of a weakly supervised framework that represents a simplified version of FIG. 5A according to some implementations.

As shown in FIG. 5A, the second measurement z may be provided as input into an inference algorithm g(•), where the inference algorithm g(•) generates an imperfect label $\tilde{y}$ as output. Generation of the imperfect label $\tilde{y}$ may occur automatically and in the background of the mobile device so as to not interfere with user experience. The inference algorithm g(•) is deterministic. Since the inference algorithm g(•) is deterministic, the graphical model can be simplified. FIG. 5B shows example conceptual model of the weakly supervised framework that represents a simplified version of FIG. 5A according to some implementations. The inference algorithm g(•) is independently trained and has an associated probability of error distribution Π that understands the performance of predicting the ground truth label y using the imperfect label S"T. The inference algorithm g(•) and its associated probability of error distribution Π are not necessarily trained or calculated by the mobile device, but the mobile device can leverage the inference algorithm g(•) and its associated probability of error distribution Π in improving a machine learning model for always-on sensing modalities.

The objective of the weakly supervised framework is to learn the statistical relationship between the first measurement x and the ground truth label y. The generative distribution p(x|y) is not accessible and can be learned using the weakly supervised framework. However, y is not an observed variable. Training set members in a training set where each training set member includes (i) a first measurement x and (ii) a ground truth label, would not be available. In other words, access to pairs $\{x_n, y_n\}_{n=1}^N$ are not given. On the contrary, training set members in a training set each includes (i) a first measurement x and (ii) an imperfect label $\tilde{y}$ representing the predicted user context, would be available. In other words, access to pairs $\{x_n, \tilde{y}_n\}_{n=1}^N$ are given. Rather than having an annotation that reflects actual user context when given an observable variable (x), the inference algorithm g(•) provides a machine automated annotation ($\tilde{y}$) that reflects predicted user context with some noise/error when given an observable variable (x).

Returning to FIG. 4, at block 440 of the process 400, a machine learning model is updated using the label $\tilde{y}$ and the first measurement x, where the one or more processors are configured to continuously predict user context using the updated machine learning model. The machine learning model may refer to a baseline model that predicts user context based only on input from the first input sensing modality group. Hence, the machine learning model may start as a simple inference algorithm or classifier that is trained, upgraded, improved, or updated by weakly supervised learning. Before learning by weakly supervised learning, the baseline model may be incorporated in the mobile device as an independently trained inference algorithm or classifier.

In some implementations, the machine learning model is updated in real-time after receiving a training instance pairing the first measurement x and the label $\tilde{y}$. The machine learning model can be improved by weakly supervised learning following a machine automated annotation with the label $\tilde{y}$ when the second input sensing modality group is opportunistically leveraged. In some implementations, the machine learning model is updated after receiving multiple stored training instances, each training instance including a pairing of a first measurement x and a label $\tilde{y}$. In other words, the machine learning model can be trained from a training set including a plurality of training set members, each training set member including: (i) stored measurements obtained from the first input sensing modality group, and (ii) stored labels of predicted user contexts obtained from measurements from the second input sensing modality group. Weakly supervised learning can be applied using the plurality of training set members after storing multiple instances of training set members on the mobile device. For example, the machine learning model can be updated when charging.

As the machine learning model is improved, the machine learning model adapts to the person using the mobile device. Though the machine learning model may start as a simple inference algorithm or classifier for a general population of users, the machine learning model is flexible so that it is continuously re-tuned for the particular user. That way, the machine learning model is personalized to the user for better performance. Since the first measurement x is typically sensitive to the user and since the second measurement z provides some contextual information (though imperfect), user-specific measurements at that moment can be paired with predicted user context. The machine learning model can be adapted for context detection that is specific to the user. By way of an example, if a user takes a subway to work, the mobile device may take a first measurement x by an audio sensor (first input sensing modality group) and a second measurement z by GPS (second input sensing modality group). The machine learning model can be trained to associate the first measurement x with taking the subway to work. If the user, however, enters an area with very poor GPS signal, then a model relying on GPS location-based data and audio sensing data would be ineffective. On the other hand, the updated machine learning model of the present disclosure would not need to rely on GPS location-based data and audio sensing data. The updated machine learning model could receive only audio sensing data and predict that the user is on the subway. Therefore, updating the machine learning model personalizes and adapts the machine learning model for the particular user in always-on sensing modalities.

In some implementations, updating the machine learning model may be performed locally on the mobile device. Updating the machine learning model does not require data or training from external or cloud-based solutions. Training the machine learning model can be done as "training on the edge" as opposed to training through outside servers and systems. In particular, weakly supervised learning can occur locally on the mobile device and the data (e.g., training set) used in weakly supervised learning can be locally stored on the mobile device. This increases data privacy and enhances information security. This also saves time and reduces network latency.

Figure 6:
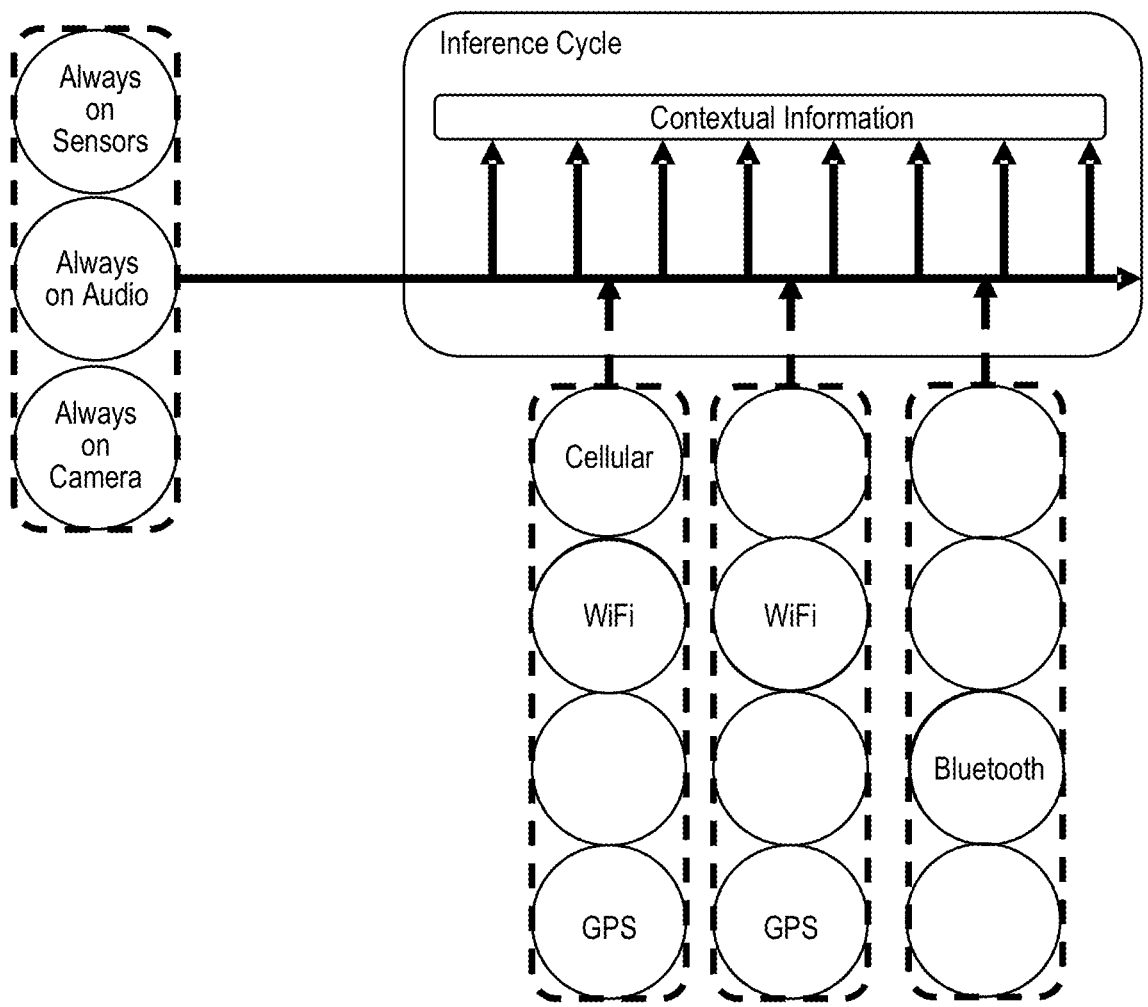
FIG. 6 shows an example diagrammatic representation of always-on sensing modalities providing context detection combined with non-always-on sensing modalities that are opportunistically leveraged, where an inference model based on always-on sensing modalities is improved over time according to some implementations.

FIG. 6 shows an example diagrammatic representation of always-on sensing modalities providing context detection combined with non-always-on sensing modalities that are opportunistically leveraged, where an inference model based on always-on sensing modalities is improved over time according to some implementations. In FIG. 6, always-on sensing modalities continuously predicts user context using a baseline model. Always-on sensing modalities may provide user-specific data or measurements from low-power sensing sources such as IMUs, audio sensors, or low-resolution cameras. As such user-specific data is tracked, predictions of user context are made over time. Non-always-on sensing modalities may be leveraged opportunistically when high-power sensing sources are available. Separate predictions of user context are made using an independently trained inference algorithm to provide a predicted user context having an associated confidence level. The predicted user context having an associated confidence level can correspond to an imperfect label ŷ having an associated probability of error distribution Π. Non-always-on sensing modalities supply contextual information with some noise, and that contextual information with some noise can train the baseline model to become more accurate. In FIG. 6, high-power sensing sources such as a cellular system, Wi-Fi system, and GPS system may supply contextual information at a first instance of a user-specific measurement. The baseline model can be trained. In a second instance of a user-specific measurement, high-power sensing sources such as a Wi-Fi system and GPS system may supply contextual information. The baseline model can be re-trained. In a third instance of a user-specific measurement, a high-power sensing source such as a Bluetooth system may supply contextual information. The baseline model can be re-trained. However, it will be understood that after collecting multiple instances of the user-specific measurements with the contextual information, the baseline model can be trained at one time. The baseline model may be trained using a weakly supervised framework as described in this present disclosure. In some implementations, the weakly supervised framework may incorporate a bias corrected probabilistic model as described in the present disclosure.

Returning to FIG. 4, the process 400 may further include repeating operations of receiving a first measurement $x_i$ from the first input sensing modality group, receiving a second measurement $z_j$ from the second input sensing modality group, determining a label $ŷ_n$ based on the second measurement $z_j$. In some implementations, the process 400 may further include updating the machine learning model using the label $ŷ_n$ and the first measurement $x_i$. The machine learning model may be continuously updated and trained over time. Improvements to the machine learning model can be observed with increased usage. An appropriate training algorithm may be used to train the machine learning model using a training set. In some implementations, a training set used by the training algorithm may include one or more training set members, each including (i) a stored measurement obtained from the first input sensing modality group, and (ii) a stored label of predicted user context obtained measurements from the second input sensing modality group. The training algorithm may be used to provide context estimation and uncertainty calculations for the predicted context based on independent variables (e.g., measurements from the first input sensing modality group) and dependent variables (e.g., noisy labels). The training algorithm may be based on one or several machine learning algorithms such as Bayesian learning. For example, Bayesian non-parametric learning adaptively trains the machine learning model by refining the detection confidence with personalization towards the particular user. Bayesian non-parametric learning is an approach for a probabilistic modeling task that views the model complexity as a random variable which is quite uncertain at the beginning (without observing any data), and gradually becomes more and more certain after seeing more data. It will be understood that the present disclosure is not limited to Bayesian learning, but may employ any suitable training algorithm known in the art. As the machine learning model is trained by the training algorithm, the trained machine learning model can more accurately predict a ground truth label y based on measurements received from the first input sensing modality group.

The goal of the machine learning model is to ascertain the generative model p(x|y), where the updated machine learning model is configured to provide a true statistical relationship p(x|y) between measurements from the first input sensing modality group and an actual user context. The generative model p(x|y) may be specific to the user associated with the mobile device. In some implementations, the machine learning model may additionally or alternatively ascertain the discriminative model p(y|x), where the updated machine learning model is configured to provide a true statistical relationship p(y|x) between an actual user context and measurements received from the first input sensing modality group. A classifier can be based on the generative model p(x|y), called a generative classifier, or based on the discriminative model p(y|x), called a discriminative classifier.

The ground truth label y is unobserved. The first measurement x is observed, the label ỹ is determined, and the associated probability of error distribution Π is provided with the label ỹ. It is possible to determine a generative distribution p(x|ỹ). Though the generative model p(x|y) is not readily known, a relationship between the generative model p(x|y) and the generative distribution p(x|ỹ) can be written as: $p(x|ỹ)=\Sigma p(x,y|ỹ)=\Sigma p(x|y)p(y|ỹ)$, where p(y|ỹ) can be represented by the confusion matrix Π. Accordingly, the generative model p(x|y) can be recovered by inverting the confusion matrix Π: $p(x|y)=\Sigma p(x|ỹ)\cdot \Pi^{-1}$. Though it is possible to determine the generative distribution p(x|ỹ), the true generative distribution p(x|ỹ) is not readily known and has to be learned through stored training instances or training set members. Stored training set members include $\{x_n, ỹ_n\}_{n=1}^N$. An estimator for p(x|ỹ) can be denoted as q(x|ỹ), and similarly an estimator for p(x|y) can be denoted as q(x|y). As used herein, a noise corrected estimator for p(x|y) can be referred to as $q(x|y=s_i)$. The noise corrected estimator can be written as: $q(x|y=s_i)=\Sigma q(x|ỹ=s_j)\cdot \Pi^{-1}$. The noise corrected estimator $q(x|y=s_i)$ gradually improves over time as more pairs of $\{x,ỹ\}$ become available. The noise corrected estimator $q(x|y=s_i)$ approximates closer to the generative model p(x|y) as the number of pairs of $\{x,ỹ\}$ increases, where the noise corrected estimator $q(x|y=s_i)$ is lossless when the number of pairs of $\{x,ỹ\}$ approaches infinity.

Updating the machine learning model in the process 400 for a generative model can include calculating the noise corrected estimator $q(x|y=s_i)$, where the noise corrected estimator is based on an inverted probability of error distribution $\Pi^{-1}$ and a plurality of stored training set members in a training set, each of the training set members include: a stored measurement obtained from the first input sensing modality group and a stored label of predicted user context obtained from a measurement from the second input sensing modality group. For example, each training set member includes a pair of $\{x,ỹ\}$ from which $q(xỹ=s_j)$ can be determined. Updating the machine learning model in the process 400 further includes retraining the machine learning model based on the noise corrected estimator $q(x|y=s_i)$. It can be shown that the noise corrected estimator $q(x|y=s_i)$ satisfies recoverability and consistency. With recoverability, the noise corrected estimator $q(x|y=s_i)$ can be shown to approximate to the generative model p(x|y) when the sample size goes to infinity. With consistency, convergence rate of the noise corrected estimator $q(x|y=s_i)$ to the ground truth is governed by the number of samples and eigenvalue structure of the confusion matrix Π.

A posterior probability can likewise be determined for a discriminative model p(y|x). It is possible to determine a discriminative distribution p(ỹ|x). Though the discriminative model is not readily known, a relationship between the discriminative model p(y|x) and the discriminative distribution p(ỹ|x) can be written as: $p(ỹ|x)=\Sigma p(y,ỹ|x)=\Sigma p(y|x)p(ỹ|y)$, where p(ỹ|y) can be represented by a right confusion matrix $\Pi_R$. Accordingly, the discriminative model p(y|x) can be recovered by inverting the right confusion matrix $\Pi_R$: $p(y|x)=\Sigma p(ỹ|x)\cdot \Pi_R^{-1}$. An estimator for p(ỹ|x) can be denoted as q(ỹ|x), and similarly an estimator for p(y|x) can be denoted as q(y|x). As used herein, a noise corrected estimator for p(y|x) can be referred to as $q(y=s_i|x)$.

Updating the machine learning model in the process 400 for a discriminative model can include calculating the noise corrected estimator $q(y=s_i|x)$, where the noise corrected estimator is based on an inverted probability of error distribution $\Pi^{-1}$ and a plurality of stored training set members in a training set, each of the training set members include: a stored measurement obtained from the first input sensing modality group and a stored label of predicted user context obtained from a measurement from the second input sensing modality group. Updating the machine learning model in the process 400 further includes retraining the machine learning model based on the noise corrected estimator $q(y=s_i|x)$.

Figure 7:
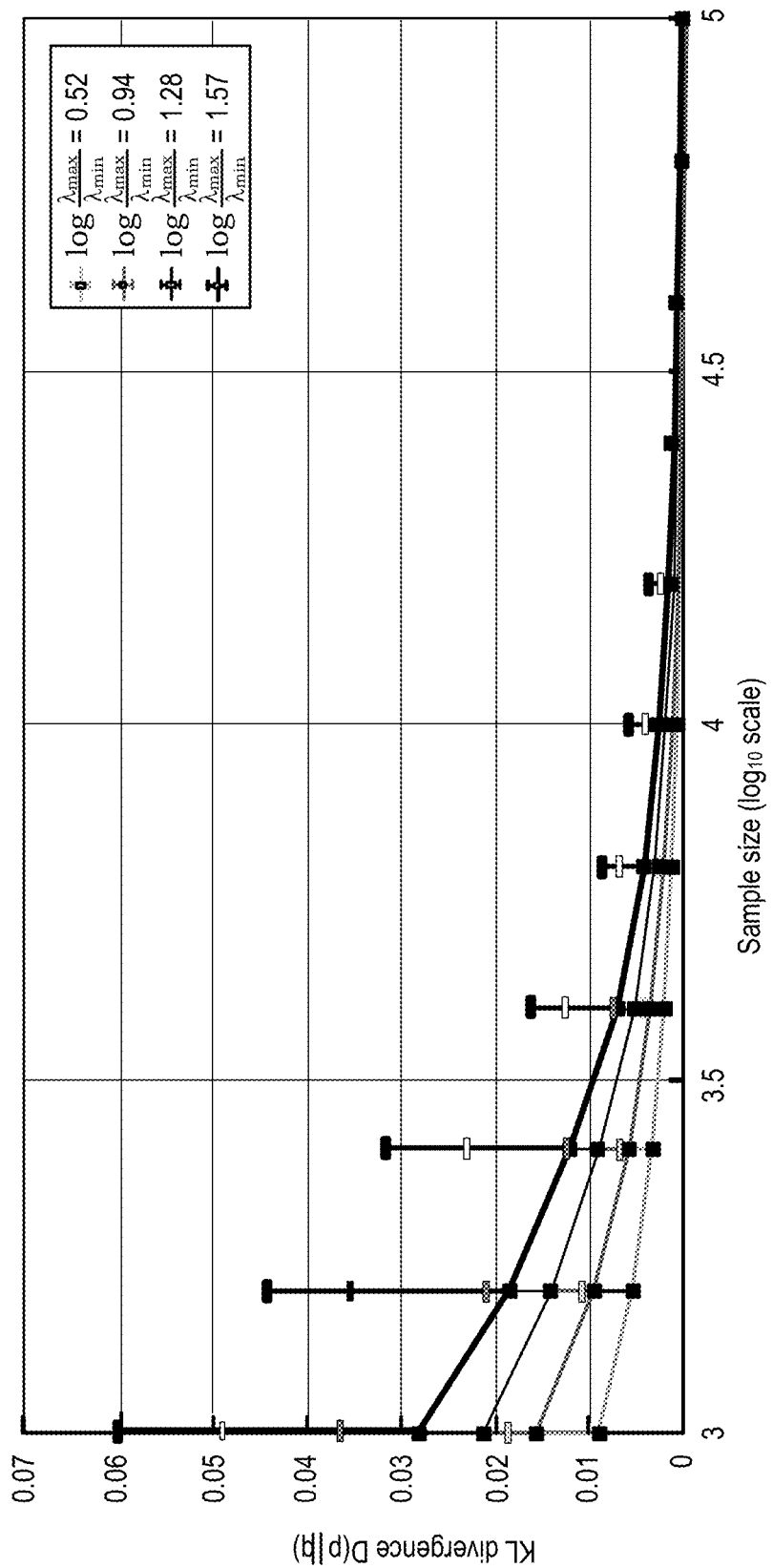
FIG. 7 shows an example plot illustrating convergence towards ground truth of inference models enhanced by noisy automated machine annotations with an increasing number of samples.

FIG. 7 shows an example plot illustrating convergence towards ground truth of inference models enhanced by noisy automated machine annotations with an increasing number of samples. The noise corrected estimator $q(x|y=s_i)$ gradually improves over time as more pairs of $\{x,ỹ\}$ become available. Thus, the noise corrected estimator $q(x|y=s_i)$ converges to the generative model p(x|y) as more pairs of $\{x,ỹ\}$ become available. The convergence rate of the noise corrected estimator $q(x|y=s_i)$ towards the generative model p(x|y) depends on the number of available pairs of $\{x,ỹ\}$ and the error, where the error can be characterized by values in the confusion matrix Π. The error reflects the distance of the current estimator to the ground truth. The convergence rate depends on the eigenvalue structure of the confusion matrix Π.

In FIG. 7, the error in the confusion matrix Π can be calculated in terms of maximum and minimum eigenvalues in the confusion matrix Π. The maximum eigenvalue is denoted $\lambda_{max}$ and the minimum eigenvalue is denoted $\lambda_{min}$. As the value of $\lambda_{max}/\lambda_{min}$ increases, the amount of error associated with the confusion matrix Π decreases. As shown in FIG. 7, higher values of $\log(\lambda_{max}/\lambda_{min})$ converge slower, as higher values of $\log(\lambda_{max}/\lambda_{min})$ require greater sample size to reach a fixed KL divergence D (p||q) value. The KL divergence D (p||q) reflects the divergence between the noise corrected estimator $q(x|y=s_i)$ and the generative distribution p(x|y).

At block 450 of the process 400, the user context is optionally predicted using the updated machine learning model at the one or more processors of the mobile device. The performance of the machine learning model gradually improves over time and with increased usage. A suitable training algorithm, such as Bayesian learning, can be applied to train the machine learning model so that the machine learning model gets closer to ground truth predictions. In some implementations, an increased number of training set members can improve the convergence rate of the machine learning model towards ground truth. In some implementations, maximum and minimum eigenvalues in the confusion matrix Π can affect the convergence rate of the machine learning model towards ground truth.

The performance of the machine learning model trained using noisy automated machine annotations (i.e., imperfect labels) can be compared against other machine learning models. Another machine learning model can include, for example, a baseline model that is separately trained beforehand for a general population of users. Yet another machine learning model can include, for example, a personalized machine learning model that is trained using user annotations. Raw data for various user activities is shown in FIGS. 8A-8B, and the performance of various machine learning models is shown in FIGS. 8C-8E.

Figure 8A:
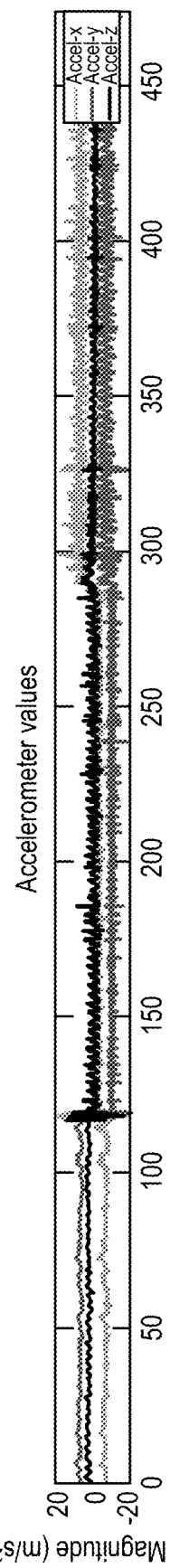
FIG. 8A shows an example plot of accelerometer data as a function of time during various user activities.

FIG. 8A shows an example plot of accelerometer data as a function of time during various user activities. FIG. 8B shows an example plot of gyroscope data as a function of time during various user activities. For about the first two minutes, a user is on the phone. After being on the phone, the user transitions to a slow walk for a little less than about three minutes. After slow walking, the user transitions to biking for a duration of about three minutes. Accelerometer data and gyroscope data show higher levels of activity after each transition in user activity.

Figure 8B:
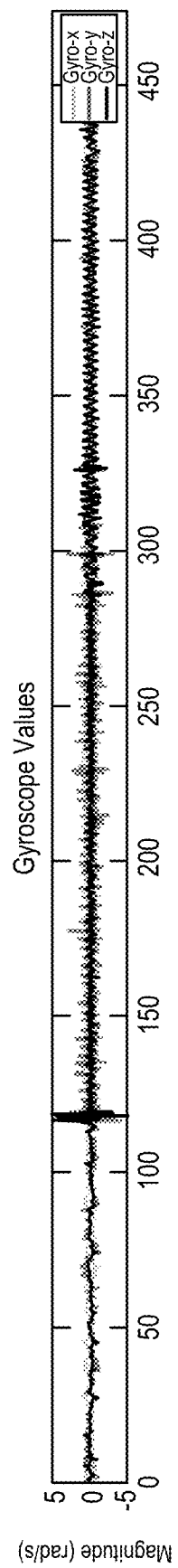
FIG. 8B shows an example plot of gyroscope data as a function of time during various user activities.
Figure 8C:
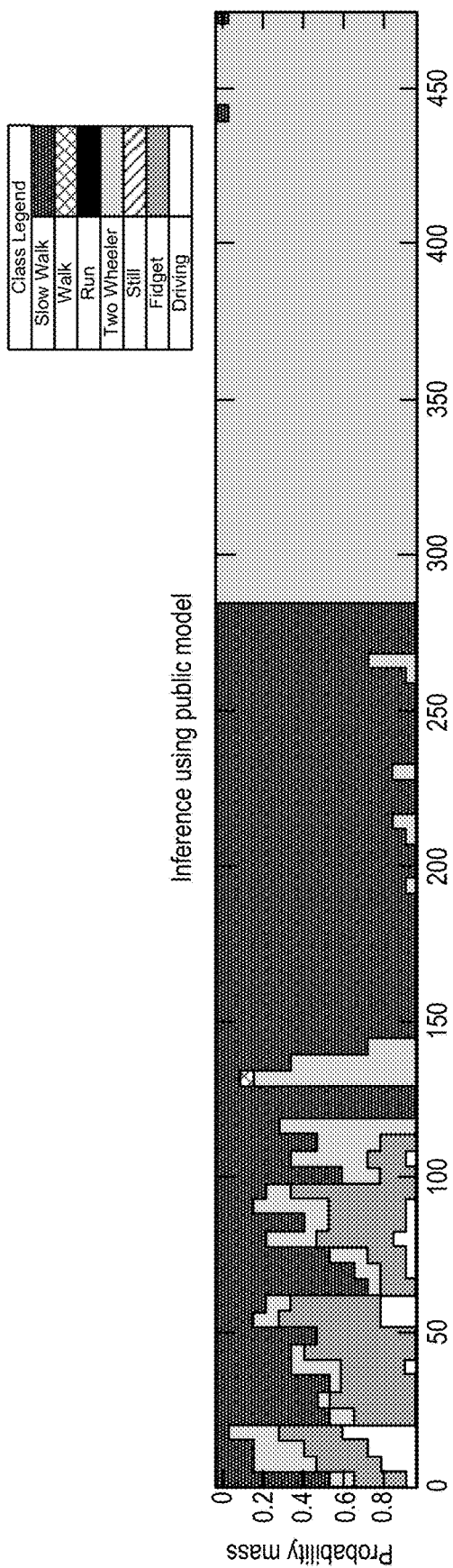
FIG. 8C shows an example plot of probability data as a function of time during the various user activities in FIGS. 8A-8B, where the probability data is determined using an independently trained inference model.

FIG. 8C shows an example plot of probability data as a function of time during the various user activities in FIGS. 8A-8B, where the probability data is determined using an independently trained inference model. The independently trained inference model can be a standard baseline model or public model applicable to a general population of users. The independently trained inference model does not learn based on user annotations or noisy machine automated annotations. As shown in FIG. 8C, the independently trained inference model does not predict making a phone call (fidgeting) with a high degree of confidence. Rather, the independently trained inference model has a hard time distinguishing between fidgeting and slow walking during the first two minutes, and also has a hard time distinguishing between biking and fidgeting. However, during the subsequent duration that is a little less than about three minutes, the independently trained inference model exhibits a moderately high level of confidence and is largely able to accurately predict slow walking. And during the remaining three minutes, the independently trained inference model demonstrates a very high level of confidence and is able to correctly predict biking.

Figure 8D:
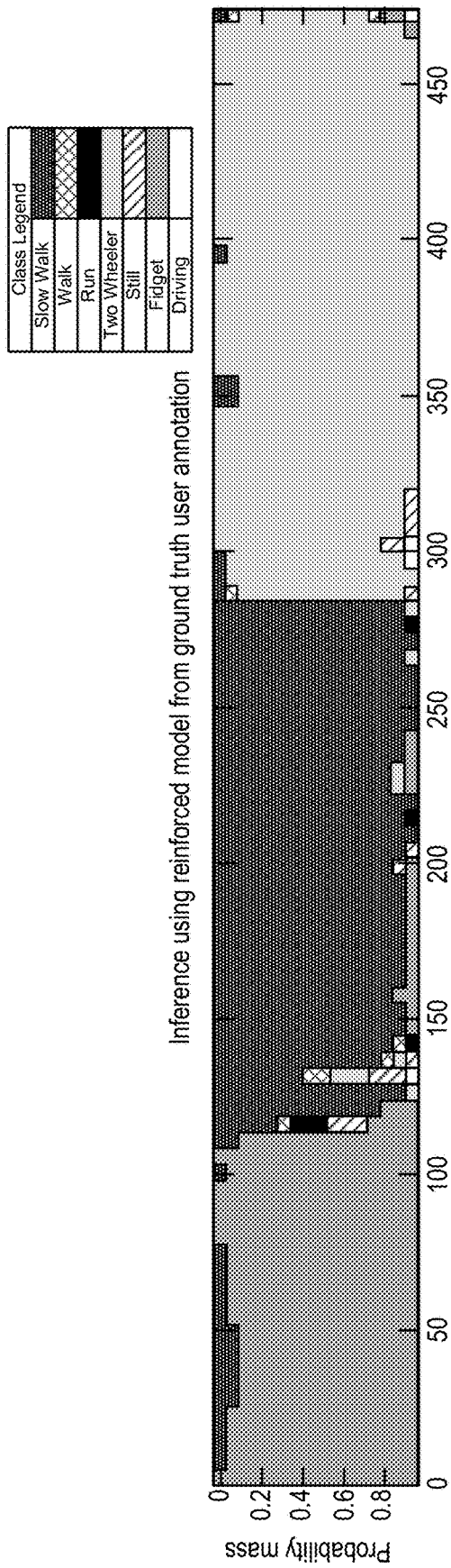
FIG. 8D shows an example plot of probability data as a function of time during the various user activities in FIGS. 8A-8B, where the probability data is determined using an inference model enhanced by user annotations.
Figure 8E:
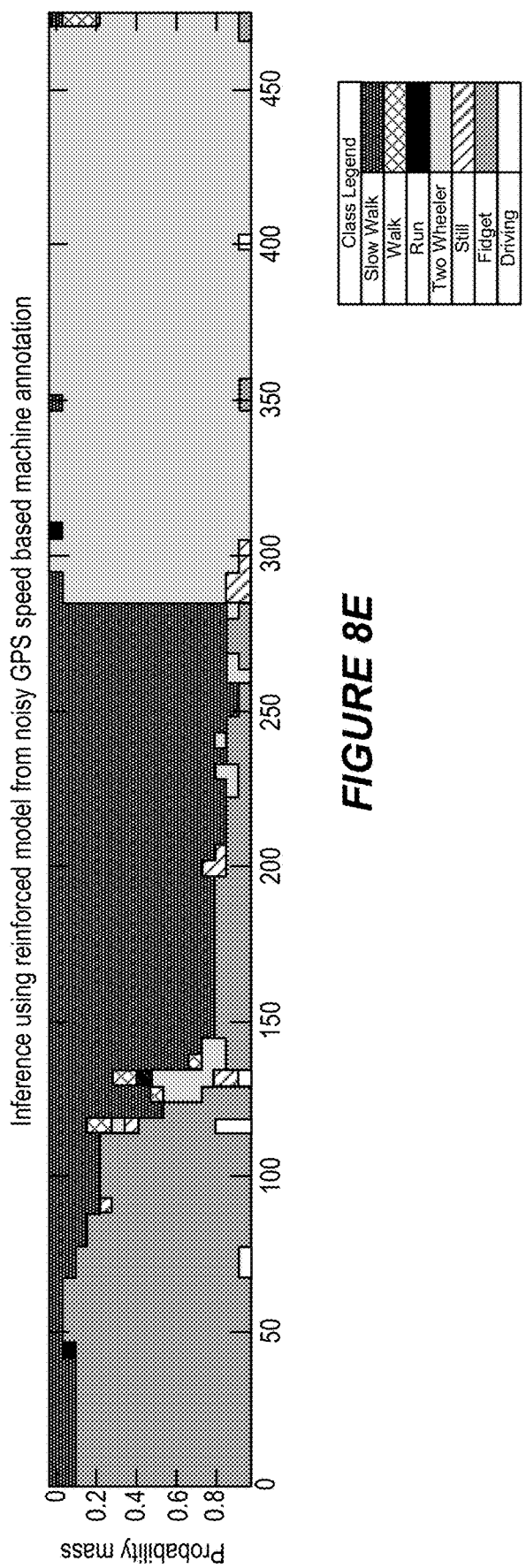
FIG. 8E shows an example plot of probability data as a function of time during the various user activities in FIGS. 8A-8B, where the probability data is determined using an inference model enhanced by noisy automated machine annotations according to some implementations.

FIG. 8D shows an example plot of probability data as a function of time during the various user activities in FIGS. 8A-8B, where the probability data is determined using an inference model enhanced by user annotation. The inference model can start as a standard baseline model that learns from user annotations. The user trains and personalizes the inference model by providing ground truth annotations so that the inference model can distinguish between different user activities. Here, the inference model enhanced by user annotations is trained for two minutes per class, meaning that the inference model is trained by collecting data for slow walking for two minutes, trained by collecting data for fidgeting for two minutes, trained by collecting data for biking for two minutes, and so forth. As shown in FIG. 8D, the inference model enhanced by user annotations effectively distinguishes between fidgeting and slow walking, and between fidgeting and biking during the first two minutes. During the remaining time, the inference model is able to accurately predict slow walking as well as biking.

FIG. 8E shows an example plot of probability data as a function of time during the various user activities in FIGS. 8A-8B, where the probability data is determined using an inference model enhanced by noisy automated machine annotation according to some implementations. The inference model can start as a standard baseline model that learns from noisy machine automated annotations as described earlier. Here, the inference model enhanced by noisy machine automated annotations is trained for two minutes per class, meaning that the inference model is trained by collecting data for slow walking for two minutes, trained by collecting data for fidgeting for two minutes, trained by collecting data for biking for two minutes, and so forth. The inference model is trained using a GPS speed-based classifier shown in Table 1, where Table 1 shows confusion statistics associated with the GPS speed-based classifier. The GPS speed-based classifier detects fidgeting when the user is traveling at speeds between about 0 mph and 0.1 mph, slow walking when the user is traveling at speeds between about 0.1 mph and 1 mph, and biking when the user is traveling between about 3 mph and about 25 mph. As shown in FIG. 8E, the inference model enhanced by noisy machine automated annotations is able to effectively distinguish between fidgeting and slow walking, and between fidgeting and biking during the first two minutes. In fact, the inference model enhanced by noisy machine automated annotations in FIG. 8E is almost as effective as the inference model enhanced by user annotations in FIG. 8D. During the remaining time, the inference model is able to accurately predict slow walking as well as biking. This shows that even after two minutes of training for different activity classes, an inference model enhanced by noisy machine automated annotations can perform very effectively in context detection. A detailed empirical Bayes error rate (BER) comparing the performances of each of the inference models in FIGS. 8C-8E is provided in Table 2.

TABLE 2

| | Model Type | | |
|---|---|---|---|
| | Baseline Model | Inference Model Enhanced by User Annotations | Inference Model Enhanced by Noisy Machine Automated Annotations |
| Bayes Error Rate | 0.22 | 0.04 | 0.05 |

The various illustrative logics, logical blocks, modules, circuits and algorithm processes described in connection with the implementations disclosed herein may be implemented as electronic hardware, computer software, or combinations of both. The interchangeability of hardware and software has been described generally in terms of functionality and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor or any conventional processor, controller, microcontroller or state machine. A processor may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, the structures disclosed in this specification and their structural equivalents thereof, or in any combination thereof. Implementations of the subject matter described in this specification may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module that may reside on a computer-readable medium. Computer-readable media include both computer storage media and communication media including any medium that may be enabled to transfer a computer program from one place to another. Storage media may be any available media that may be accessed by a computer. By way of example and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein.

Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

What is claimed is:

1. A method of improving a machine learning model for use in context detection, the method comprising:
    receiving, at one or more processors of a mobile device, a first measurement x from a first input sensing modality group of the mobile device, wherein the first input sensing modality group includes a low-power sensing source;
    receiving, at one or more processors of the mobile device, a second measurement z from a second input sensing modality group of the mobile device, wherein the second input sensing modality group includes a high-power sensing source;
    determining, at the one or more processors of the mobile device, a label $\hat{y}$ based on the second measurement z, wherein the label $\hat{y}$ represents a predicted user context having an associated probability of error distribution $\Pi$, wherein the associated probability of error distribution $\Pi$ reflects a probability of error in statistics between the label $\hat{y}$ and an actual user context y; and
    updating a machine learning model using the label $\hat{y}$ and the first measurement x, wherein the one or more processors are configured to continuously predict user context using the updated machine learning model.

2. The method of claim 1, wherein the high-power sensing source is selected from a group consisting of: a high-resolution camera, a global positioning system (GPS), a cellular system, a Wi-Fi system, and a Bluetooth system.

3. The method of claim 1, wherein the low-power sensing source is selected from a group consisting of: an accelerometer, a gyroscope, a magnetometer, a light sensor, a proximity sensor, a low-resolution camera, a microphone or an audio sensor, an electrocardiogram (ECG), a photoplethysmogram (PPG), a temperature sensor, a respiration sensor, a compass, and a barometer.

4. The method of claim 1, wherein determining the label $\hat{y}$ based on the second measurement z is determined using an independently trained inference model or classifier, wherein the independently trained inference model or classifier comprises the associated probability of error $\Pi$, wherein the independently trained inference model or classifier is a deterministic algorithm for measurements obtained from the second input sensing modality group.

5. The method of claim 1, wherein the machine learning model is configured to provide a true statistical relationship p(x|y) between measurements received from the first input sensing modality group and an actual user context.

6. The method of claim 5, wherein updating the machine learning model comprises:
    calculating, at the one or more processors of the mobile device, a noise corrected estimator $q(x|y=s_i)$, wherein the noise corrected estimator $q(x|y=s_i)$ is based on an inverted probability of error distribution $\Pi^{-1}$ and a plurality of stored training set members in a training set, the plurality of stored training set members comprising: (i) stored measurements obtained from the first input sensing modality group of the mobile device, and (ii) stored labels of predicted user contexts obtained from measurements from the second input sensing modality group of the mobile device; and retraining the machine learning model based on the noise corrected estimator $q(x|y=s_i)$.

7. The method of claim 6, wherein the noise corrected estimator $q(x|y=s_i)$ approximates closer to the true statistical relationship $p(x|y)$ between measurements received from the first input sensing modality group and the actual user context with an increasing number of stored training set members in the training set.

8. The method of claim 1, wherein the machine learning model is configured to provide a true statistical relationship $p(y|x)$ between an actual user context and measurements received from the first input sensing modality group.

9. The method of claim 8, wherein updating the machine learning model comprises:

calculating, at the one or more processors of the mobile device, a noise corrected estimator $q(y=s_i|x)$, wherein the noise corrected estimator $q(y=s_i|x)$ is based on an inverted probability of error distribution $\Pi^{-1}$ and a plurality of stored training set members in a training set, the plurality of stored training set members comprising: (i) stored measurements obtained from the first input sensing modality group of the mobile device, and (ii) stored labels of predicted user contexts obtained from measurements from the second input sensing modality group of the mobile device; and retraining the machine learning model based on the noise corrected estimator $q(y=s_i|x)$.

10. The method of claim 9, further comprising:

predicting, via the one or more processors of the mobile device, a user context using the retrained machine learning model.

11. The method of claim 10, wherein user context is selected from a group consisting of: a physical activity, a transportation mode, an acoustic environment, a mood, and a health condition.

12. The method of claim 1, further comprising:

storing the first measurement x and the label $\tilde{y}$ locally on the mobile device as a training set member in a training set, wherein updating the machine learning model is performed locally on the mobile device.

13. The method of claim 1, wherein updating the machine learning model occurs without user annotation.

14. The method of claim 1, wherein updating the machine learning model comprises:

adapting the machine learning model to be personal to a user associated with the mobile device.

15. A mobile device comprising:

a low-power sensing source configured to provide a first measurement x;

a high-power sensing source configured to provide a second measurement z;

one or more processors coupled to the low-power sensing source and to the high-power sensing source, wherein the one or more processors are configured to:

receive the first measurement x from the low-power sensing source;

receive the second measurement z from the high-power sensing source;

determine a label $\tilde{y}$ based on the second measurement z, wherein the label $\tilde{y}$ represents a predicted user context having an associated probability of error distribution $\Pi$, wherein the associated probability of error distribution $\Pi$ reflects a probability of error in statistics between the label $\tilde{y}$ and an actual user context y; and update a machine learning model using the label $\tilde{y}$ and the first measurement x.

16. The mobile device of claim 15, wherein the one or more processors are further configured to:

continuously predict user context using the updated machine learning model.

17. The mobile device of claim 15, wherein the high-power sensing source is selected from a group consisting of: a high-resolution camera, a global positioning system (GPS), a cellular system, a Wi-Fi system, and a Bluetooth system, wherein the low-power sensing source is selected from a group consisting of: an accelerometer, a gyroscope, a magnetometer, a light sensor, a proximity sensor, a low-resolution camera, a microphone or an audio sensor, an electrocardiogram (ECG), a photoplethysmogram (PPG), a temperature sensor, a respiration sensor, a compass, and a barometer.

18. The mobile device of claim 15, wherein the one or more processors are further configured to:

store the first measurement x and the label $\tilde{y}$ locally on the mobile device as a training set member in a training set.

19. The mobile device of claim 15, wherein the one or more processors configured to determine the label $\tilde{y}$ based on the second measurement z is configured to determine the label $\tilde{y}$ using an independently trained inference model or classifier, wherein the independently trained inference model or classifier comprises the associated probability of error $\Pi$, wherein the independently trained inference model or classifier is a deterministic algorithm for measurements obtained from the second input sensing modality group.

* * * * *